United States Patent [19]

Dockner et al.

[11] Patent Number: 4,602,927
[45] Date of Patent: Jul. 29, 1986

[54] 4-ALKYLIMIDAZOLE DERIVATIVES AND THEIR USE AS NITRIFICATION INHIBITORS

[75] Inventors: Toni Dockner, Meckenheim; Ernst-Heinrich Pommer, Limburgerhof; Jüergen Dressel, Neuhofen, all of Fed. Rep. of Germany

[73] Assignee: BASF Aktiengesellschaft, Ludwigshafen, Fed. Rep. of Germany

[21] Appl. No.: 642,204

[22] Filed: Aug. 20, 1984

[30] Foreign Application Priority Data

Aug. 20, 1983 [DE] Fed. Rep. of Germany ....... 3330192

[51] Int. Cl.$^4$ ..................... C09K 17/00; C07D 233/54
[52] U.S. Cl. ............................................. 71/1; 71/30; 71/64.01; 71/902; 548/337
[58] Field of Search ............... 548/337; 71/902, 64.01, 71/30, 1

[56] References Cited

U.S. PATENT DOCUMENTS 3,996,366 12/1976 Baker et al. ..................... 548/337 X
4,233,058 11/1980 Sasse et al. ............................. 71/92
4,314,844 2/1982 Swithenbank et al. ......... 548/337 X

FOREIGN PATENT DOCUMENTS 2745833 4/1979 Fed. Rep. of Germany ...... 548/376

Primary Examiner—Richard A. Schwartz
Attorney, Agent, or Firm—Keil & Weinkauf

[57] ABSTRACT

4-Alkylimidazole derivatives of the formula I

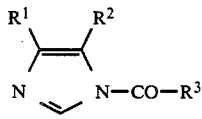

where $R^1$ is $C_1$–$C_4$-alkyl, $R^2$ is chlorine or bromine and $R^3$ is an —$OR^4$ or —$NR^5R^6$ group in which $R^4$ is $C_1$–$C_4$-alkyl, $R^5$ is hydrogen or $C_1$–$C_4$-alkyl and $R_6$ is $C_1$–$C_4$-alkyl or is phenyl which is unsubstituted or substituted by 1 or 2 halogen atoms, and its salts, their preparation and their use as nitrification inhibitors.

3 Claims, No Drawings

4-ALKYLIMIDAZOLE DERIVATIVES AND THEIR USE AS NITRIFICATION INHIBITORS

The present invention relates to novel 4-alkylimidazole derivatives and their use as nitrification inhibitors.

Ammonium nitrogen in the soil is oxidized via nitrite nitrogen to nitrate nitrogen by bacteria of the genera Nitrosomonas and Nitrobacter. The extent of nitrification depends on the type, pH, moisture content and biological activity of the soil. In contrast to the ammonium nitrogen, the nitrate nitrogen can be washed out, especially in fairly light soils, and is therefore no longer available for plant nutrition, and there is a danger of the groundwater becoming enriched with nitrate, so that the inhibition of nitrification is particularly important.

Examples of commercial products used for this purpose are dazomet (3,5-dimethyltetrahydro-1,3,5-thiadiazine-2-thione), nitrapyrin (2-chloro-6-trichloromethylpyridine, cf. Down to Earth 32 (1976), 14–17) and dicyanodiamide (Landw. Forschung 27 (1972), 74–82). Certain pyrimidine and pyrazole derivatives are also said to act as nitrification inhibitors (cf. German Laid-Open Application DOS 2,745,833). However, the conventional active ingredients do not meet all requirements with regard to efficiency, selectivity, duration of action, cost effectiveness, lack of harmful properties and performance characteristics such as water-solubility, dispersibility, vapor pressure, etcetera.

We have found that 4-alkylimidazole derivatives of the formula I

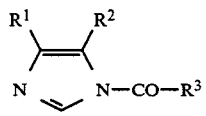   I where $R^1$ is $C_1$–$C_4$-alkyl, $R^2$ is chlorine or bromine, and $R^3$ is an —$OR^4$ or —$NR^5R^6$ group, in which $R^4$ is $C_1$–$C_4$-alkyl, $R^5$ is hydrogen or $C_1$–$C_4$-alkyl and $R^6$ is $C_1$–$C_4$-alkyl or is phenyl which is unsubstituted or substituted by 1 or 2 halogen atoms, and their salts possess good properties as nitrification inhibitors.

In formula I, $R^1$ is preferably methyl, $R^2$ is preferably chlorine and $R^3$ is preferably an $NR^5R^6$ group in which $R^5$ is preferably hydrogen and $R^6$ is preferably methyl, or phenyl which is unsubstituted or substituted by 1 or 2 chlorine atoms.

The novel 4-alkylimidazole derivatives can be obtained by a method in which (a) where $R^3$ is an $OR^4$ or $NR^5R^6$ group in which $R^5$ is $C_1$–$C_4$-alkyl, a compound of the formula II

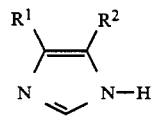   II where $R^1$ and $R^2$ have the above meanings, is reacted with a compound of the formula III

X—CO—$R^3$   III where $R^3$ has the above meanings and X is halogen, in the presence of a base or (b) where R is $NHR^6$, a compound of the formula II is reacted with an isocyanate of the formula IV

   IV where $R^3$ has the above meanings.

From a consideration of formula I, a number of other possible methods of preparation will directly become apparent to the skilled worker, and these possible methods will not be discussed here.

Reaction (a) is carried out as a rule in the presence of an equivalent amount of base. Particularly suitable bases are tertiary amines, eg. trimethylamine or triethylamine, and alkali metal and alkaline earth metal hydroxides and alcoholates. Examples of suitable solvents are chloroform, toluene, xylene and chlorobenzenes. The reaction takes place as a rule at from 40° to 100° C., and is advantageously carried out at the reflux temperature of the solvent used.

Reaction (b) is carried out in a solvent which is inert under the reaction conditions, particularly suitable solvents of this type being hydrocarbons and halohydrocarbons boiling within a range from 40° to 140° C., preferably from 60° to 110° C., acetonitrile and dimethylformamide. The reaction takes place as a rule under reflux conditions.

The starting materials of the formula II which are required for the reactions are obtainable by reacting the corresponding imidazoles with halogen or a hypohalite (cf. German Laid-Open Application DOS 3,145,927).

The substances according to the invention can be used as such, ie. as the free (very weak) bases, or as a salt of a biologically acceptable acid, preferably as the phosphate, sulfate, acetate, citrate, tartrate or, in particular, hydrochloride, either alone or as a mixture with solid or liquid fertilizers which contain ammonium nitrogen, urea or ammonia. Application together with crop treatment agents or soil conditioners is also possible. Advantageously, the active ingredients are applied simultaneously with the fertilizer. The amounts applied are from 0.05 to 10, preferably from 0.5 to 3, kg/ha. Where they are used in combination with solid or liquid fertilizers, the active ingredients can be employed in amounts of from about 0.5 to 10 percent by weight, based on fertilizer nitrogen.

The novel nitrification inhibitors are very effective, non-toxic, non-volatile, sufficiently water-soluble and stable. They remain in the soil for a long time and are therefore effective over a long period. Hence, they not only protect the environment by preventing nitrate from being washed out into the groundwater, but also permit substantially better utilization of fertilizer, in particular in fairly light soils.

EXAMPLE 1

104 g of methyl isocyanate were added dropwise to 233 g of 4-methyl-5-chloroimidazole in 1 liter of chloroform in a stirred flask provided with a thermometer and a reflux condenser. During the addition, the temperature increased to 40° C. Refluxing was carried out for 2 hours, the reaction solution was evaporated down under reduced pressure, the hot residue was dissolved in 400 ml of toluene, the solution was filtered with carbon and cooled, and the precipitated crystals were filtered off under suction, washed with toluene and dried to give 237 g (68.3%) of 1-N-methylcarbamyl-4-methyl-5-chloroimidazole of melting point 94.1°–94.4° C.

EXAMPLE 2

76 g of triethylamine and, thereafter, 68 g of diethylcarbamyl chloride were added dropwise to 58.5 g of 4-methyl-5-chloroimidazole in 200 ml of chloroform in a stirred flask provided with a thermometer and reflux condenser. Refluxing was then carried out for 2 hours, after which the mixture was cooled and the precipitated triethylamine hydrochloride was filtered off under suction. The filtrate was evaporated down under reduced pressure, 500 ml of acetone was added to the residue, and HCl gas was passed in while the mixture was cooled with ice. The resulting precipitate was filtered off under suction and dried to give 66 g (52.4%) of 1-N-diethylcarbamyl-4-methyl-5-chloroimidazole hydrochloride; mp. from 208° C., with decomposition.

EXAMPLE 3

Using a procedure similar to that described in Example 1, 59.5 g of phenyl isocyanate were added dropwise to 58.5 g of 4-methyl-5-chloroimidazole in 250 ml of chloroform. During the addition, the temperature increased to 42° C. Refluxing was then carried out for 2 hours, after which the solution was cooled with ice, and the precipitate which separated out was filtered off under suction, washed with chloroform and dried to give 80 g (67.9%) of 1-N-phenylcarbamyl-4-methyl-5-chloroimidazole of melting point 112.3°–114.4° C.

EXAMPLE 4

Using a procedure similar to that described in Example 1, a solution of 47 g of 3,4-dichlorophenyl isocyanate in 50 g of chloroform was added dropwise to 29 g of 4-methyl-5-chloroimidazole in 150 g of chloroform. Refluxing was carried out for 2 hours, after which the solution was cooled and the resulting precipitate was filtered off under suction and dried to give 60 g (78.9%) of 1-N-(3,4-dichlorophenyl)-carbamyl-4-methyl-5-chloroimidazole of melting point 143.7°–144.7° C.

EXAMPLE 5

Using a procedure similar to that described in Example 1, a solution of 47 g of 3,5-dichlorophenyl isocyanate in 100 ml of chloroform was added dropwise to 29 g of 4-methyl-5-chloroimidazole, likewise dissolved in 100 ml of chloroform. Refluxing was carried out for 2 hours, after which the solution was cooled and the residue was filtered off under suction, washed with chloroform and dried to give 60 g (78.8%) of 1-N-(3,5-dichlorophenylcarbamyl)-4-methyl-5-chloroimidazole of melting point 136.9°–138.6° C.

EXAMPLE 6

Using a procedure similar to that described in Example 1, 13 g of methyl isocyanate were added dropwise to 40 g of 4-methyl-5-bromoimidazole in 200 ml of chloroform. During the addition, the temperature increased to 35° C. Refluxing was carried out for 2 hours, after which the reaction solution was evaporated down under reduced pressure to give 55 g of residue, which was recrystallized from 110 ml of toluene. The crystals were cooled, and the product was filtered off under suction and dried to give 30 g (55%) of 1-[N-methylcarbamyl]-4-methyl-5-bromoimidazole of melting point 98.4°–100.1° C.

EXAMPLE 7

Using a procedure similar to that described in Example 1, 582.5 g of 4-methyl-5-chloroimidazole were dissolved in 1,500 ml of toluene at 70° C., and 313.5 g of methyl isocyanate were slowly run into the solution. During the addition, the temperature increased to about 90° C. Refluxing was then carried out for 30 minutes, after which the solution was cooled and then stirred for a further hour while being cooled with ice, and the precipitate which separated out was filtered off under suction, washed with ether and dried to give 826 g (95.2%) of 1-N-methylcarbamyl-4-methyl-5-chloroimidazole of melting point 95.6° C.

EXAMPLE 8

58.5 g of 4-methyl-5-chloroimidazole were dissolved in 200 ml of chloroform in a stirred apparatus as described in Example 1. 76 g of triethylamine were added, and 54.5 g of ethyl chloroformate were added dropwise through a dropping funnel. During the addition, the temperature increased to the boiling point.

Refluxing was then carried out for 2 hours, after which the solution was cooled to 0° C., and the precipitated triethylamine hydrochloride was filtered off under suction (53 g).

The filtrate was evaporated down under reduced pressure to give an oily residue, some of which crystallized. This residue was digested in acetone, and solid material was filtered off under suction and dried. In this manner, a further 15 g of triethylamine hydrochloride were obtained. The filtrate was once again evaporated down under reduced pressure, and the residue was distilled to give 64 parts (68% of theory) of 1-ethoxycarbonyl-4-methyl-5-chloroimidazole (bp. 92° C./40 Pa).

USE EXAMPLE 220 mg of ammonium sulfate were mixed thoroughly with 200 g of a loamy sandy soil whose moisture content had been brought to 50% of the maximum water capacity. The active ingredients, dissolved in 0.2 ml of acetone, were then added in amounts of 1 ppm, based on moist soil. After careful, thorough mixing, and evaporation of the acetone, the soil samples were incubated for 28 days at 21° C., together with the controls without added active ingredient, 1 liter glass vessels covered with aluminum foil to avoid loss of water.

2.5 g of each of the soil samples were then introduced into 100 ml conical flasks, and 22.5 ml of a 0.1N sodium sulfate solution was added. The flask was shaken for 30 minutes, after which the mixture was filtered, and 2.5 ml samples of the soil extracts were mixed with 1,625 ml of distilled water. To detect the ammonium ions still present in the soil extract, 1.25 ml of Nessler reagent were then added, and the mixture was shaken thoroughly. The color changes were then measured photometrically at a wavelength of 420 nm. The amounts of ammonium sulfate still present in the soil samples were then determined with reference to standard curves obtained by a measurement of solutions containing known amounts of ammonium sulfate. The percentage inhibition of nitrification in the treated soil samples compared with the untreated soil samples (to which only ammonium sulfate had been added) was calculated using the following formula:

$$\ldots \% \text{ inhibition of nitrification} = \frac{a-b}{a} \cdot 100$$

a = nitrification rate for ammonium sulfate
b = nitrification rate for ammonium sulfate + nitrification inhibitor The Table below shows the results obtained. The comparative substance (A) used was substance No. 95 (1-phenoxycarbamyl-3-methylpyrazole) described in German Laid-Open Application DOS 2,745,833.

| Active ingredient from Example | % inhibition of nitrification 4 weeks after the addition of 1 ppm of active ingredient to the soil |
|---|---|
| 1 | 94 |
| 3 | 85 |
| 4 | 71 |
| A | 69 |

We claim:

1. A member selected from the group consisting of 4-alkylimidazole derivative of the formula I

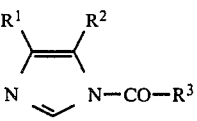

where $R^1$ is $C_1$–$C_4$-alkyl, $R^2$ is chlorine or bromine, and $R^3$ is an —$OR^4$ or —$NR^5R^6$ group in which $R^4$ is $C_1$–$C_4$-alkyl, $R^5$ is hydrogen or $C_1$–$C_4$-alkyl and $R^6$ is $C_1$–$C_4$-alkyl or is phenyl which is unsubstituted or substituted by 1 or 2 halogen atoms, and its salt of a biologically acceptable acid.

2. A process for inhibiting the nitrification of ammoniun nitrogen in the soil, wherein from 0.05 to 10 kg/ha of a compound of the formula or its salt of a biologically acceptable acid as claimed in claim 1 is introduced into the soil.

3. A nitrification inhibitor composition, containing a compound of the formula I or its salt of a biologically acceptable acid as claimed in claim 1.

* * * * *